US007560282B2

(12) United States Patent
Gerdes

(10) Patent No.: US 7,560,282 B2
(45) Date of Patent: Jul. 14, 2009

(54) SYSTEM FOR THE INTERNAL QUALITATIVE AND QUANTITATIVE VALIDATION OF MARKER INDICES

(75) Inventor: Johannes Gerdes, Feldhorst (DE)

(73) Assignee: DakoCytomation Denmark A/S, Glostrup (DK)

( * ) Notice: Subject to any disclaimer, the term of this patent is extended or adjusted under 35 U.S.C. 154(b) by 652 days.

(21) Appl. No.: 10/182,013

(22) PCT Filed: Jan. 23, 2001

(86) PCT No.: PCT/EP01/00717

§ 371 (c)(1), (2), (4) Date: Sep. 19, 2002

(87) PCT Pub. No.: WO01/55346

PCT Pub. Date: Aug. 2, 2001

(65) Prior Publication Data

US 2003/0124563 A1 Jul. 3, 2003

(30) Foreign Application Priority Data

Jan. 24, 2000 (DE) ................................. 100 02 803

(51) Int. Cl.
*G01N 31/00* (2006.01)
(52) U.S. Cl. ........................... 436/15; 435/1.1; 435/1.2; 435/2; 435/7.2; 435/40.51; 435/40.52; 435/325; 435/347; 435/365.1; 435/367; 435/368; 435/369; 435/370; 435/371; 435/372; 436/501; 436/530; 436/546; 436/10; 436/18; 436/63; 436/174; 436/176
(58) Field of Classification Search .................. 435/1.1, 435/1.2, 1.3, 2, 7.2, 7.21–7.32, 7.92, 40.5, 435/325, 40.52, 334–336, 347, 373, 378, 435/397, 284.1, 40.51, 70.1, 365.1–372.3, 435/287.6, 287.1; 436/501, 524, 528, 546, 436/15, 18, 63, 174, 176, 530, 10, 46
See application file for complete search history.

(56) References Cited

U.S. PATENT DOCUMENTS

| 5,478,739 | A | * | 12/1995 | Slivka et al. | .................. | 435/399 |
| 5,610,022 | A | * | 3/1997 | Battifora | ..................... | 435/7.23 |
| 6,281,004 | B1 | * | 8/2001 | Bogen et al. | ............. | 435/287.1 |
| 2002/0120098 | A1 | * | 8/2002 | Bell et al. | .................... | 530/300 |

FOREIGN PATENT DOCUMENTS

| EP | 0695760 A1 | 2/1996 |
| WO | WO 98/08976 | 3/1998 |

OTHER PUBLICATIONS

Chan et al., The potential of oncogene products as tumour markers, Cancer Surveys 6 (2): 185-207 (1987). Abstract Only.*

Borre, M. et al., "Tumor Cell Proliferation and Survival in Patients with Prostate Cancer Followed Expectantly," *The Journal of Urology*, 159:1609-1614 (1998).

Clahsen, P.C. et al., "p53 Protein Accumulation and Response to Adjuvant Chemotherapy in Premenopausal Women with Node-Negative Early Breast Cancer," *J. of Clinical Oncology*, 16(2):470-479 (1998).

Coetzee, L.J. et al., "Proliferative Index Determination in Prostatic Carcinoma Tissue: Is There any Additional Prognostic Value Greater than that of Gleason Score, Ploidy and Pathological Stage?," *The Journal of Urology*, 157:214-218 (1997).

Gerdes, J. et al., "Prognostic Relevance of Tumour-Cell Growth Fractions in Malignant Non-Hodgkin's Lymphomas," *The Lancet*, 2(8556):448-449 (1987).

Gerdes, J. et al., "Production of a Mouse Monoclonal Antibody Reactive with a Human Nuclear Antigen Associated with Cell Proliferation," *Int. J. Cancer*, 31:13-20 (1983).

Gerdes, J. et al., "Cell Cycle Analysis of a Cell Proliferation-Associated Human Nuclear Antigen Defined by the Monoclonal Antibody Ki-67," *The Journal of Immunology*, 133(4):1710-1715 (1984).

Grogan, T.M. et al., "Independent Prognostic Significance of a Nuclear Proliferation Antigen in Diffuse Large Cell Lymphomas as Determined by the Monoclonal Antibody Ki-67," *Blood*, 71(4):1157-1160 (1988).

Hall, P.A. et al., "The Prognostic Value of Ki67 Immunostaining in Non-Hodgkin's Lymphoma," *Journal of Pathology*, 154:223-235 (1988).

Jansen, R.L.H. et al., "MIB-1 Labelling Index is an Independent Prognostic Marker in Primary Breast Cancer," *British Journal of Cancer*, 78(4):460-465 (1998).

Lellé, R.J. et al., "The Correlation of Growth Fractions with Histologic Grading and Lymph Node Status in Human Mammary Carcinoma," *Cancer* 59:83-88 (1987).

Lokhorst, H.M. et al., "Novel Type of Proliferating Lymphoplasmacytoid Cell with a Charateristic Spotted Immunofluorescence Pattern," *J. Clin. Invest.*, 79:1401-1411 (1987).

Molino, A. et al., "Ki-67 Immunostaining in 322 Primary Breast Cancers: Associations with Clinical and Pathological Variables and Prognosis," *J. Cancer (Pred. Oncol.)*, 74:433-437 (1997).

Querzoli, P. et al., "MIB-1 Proliferative Activity in Invasive Breast Cancer Measured by Image Analysis," *J. Clin. Pathol.*, 49:926-930 (1996).

Rozan, S. et al., "No Significant Predictive Value of c-*erb*B-2 or *p53* Expression Regarding Sensitivity to Primary Chemotherapy or Radiotherapy in Breast Cancer," *Int. J. Cancer (Pred. Oncol.)*, 79:27-33 (1998).

(Continued)

*Primary Examiner*—Gailene R Gabel
(74) *Attorney, Agent, or Firm*—Hamilton, Brook, Smith & Reynolds, P.C.

(57) ABSTRACT

The present invention relates to the qualitative and quantitative validation of marker indices, especially for medical diagnosis and particularly for the determination of the growth fraction in a sample with antibodies against the Ki-67 protein. Diagnostic kit for the quantification of a cell fraction labeled by a marker for in vitro diagnosis, characterized in that a pseudo-tissue is used for the intra- and inter-assay standardization of the marker index.

36 Claims, 3 Drawing Sheets

OTHER PUBLICATIONS

Sawhney, N. et al., "Ki67—Structure, Function, and New Antibodies," *Journal of Pathology*, 168:161-162 (1992).

Schwarting, R. et al., "Little Missed Markers and Ki-67," *Lab. Invest.*, 68(6):597-599 (1993).

Uzoaru, I. et al., "An Evaluation of the Marker p53 and Ki-67 for their Predictive Value in Prostate Cancer," *Journal of Surgical Oncology*, 67:33-37 (1998).

Veronese, S.M. et al., "Comparative Prognostic Value of Ki-67 and MIB-1 Proliferation Indices in Breast Cancer," *Anticancer Research*, 16:2717-2722 (1996).

Aaltoma, S. et al., "Value of Ki-67 Immunolabelling as a Prognostic Factor in Prostate Cancer," *Eur. Urol.*, 32:410-415 (1997).

Gerdes, J. et al., "Growth Fractions and Estrogen Receptors in Human Breast Cancers as Determined in Situ with Monoclonal Antibodies," *American Journal of Pathology*, 129(3):486-492 (1987).

Gerdes, J. et al., "Tumor Cell Growth Fraction in Hodgkin's Disease," *American Journal of Pathology*, 128(3):390-393 (1987).

Harbeck, N. et al., "Multivariater Vergleich Neuerer Tumorbiologischer Prognosefaktoren (unter Einschluβ von S-Phase und MIB1) beim nodalnegativen Mammakarzinom," In Prognostic and Relevant Therapy Factors In Breast Cancer, Novartis Pharma Publishers, Nuremberg, pp. 91-100 (1997). (English language translation).

\* cited by examiner

Inter-observer variability (average values, series 1)

Inter observer variability (average values, series 2)

Inter-assay variability

SYSTEM FOR THE INTERNAL QUALITATIVE AND QUANTITATIVE VALIDATION OF MARKER INDICES

RELATED APPLICATIONS

This application is the U.S. National stage of International Application No. PCT/EP01/00717, filed on Jan. 23, 2001, published in English, which claims priority under 35 U.S.C. § 119 or 365 to German Application No. DE 100 02 803.9, filed Jan. 24, 2000. The entire teachings of the above applications are incorporated herein by reference.

TECHNICAL FIELD

The present invention relates to a tool for use in the qualitative and quantitative validation of marker indices, especially for medical diagnosis, prognosis and therapeutic relevance such as for the determination of the growth fraction in a sample with antibodies against the Ki-67 protein.

BACKGROUND ART

The determination of markers and marker indices is an integral component of modern medical diagnosis in most varied medical fields. Hence, for example, the determination of the relationship of high density lipoproteins (HDL) to low-density lipoproteins (LDL) is part of the routine for blood tests; the determination of the relationship of CD4 to CD8 positive blood cells is one of the most important parameters of AIDS diagnosis; in the diagnosis of tumors, for example breast cancer, the determination of the hormone receptor status is considered to be an indicator for treatment following an operation. Because most varied structures serve as markers, the methods of determination are also diverse: ELISA, RIA, chemical and/or biochemical titrations, FACS, luminometric, nephelometric, densitometric analyses, etc. which are well known to the skilled person.

In the diagnosis of tumors, thin tissue section examination and/or cytological examination of a sample is still the method of choice. For this purpose, the trained pathologist applies histochemical and immunohistochemical and/or cytochemical and immunocytochemical methods to an increasing degree. Thus, the hormone receptor status mentioned above is immunohistologically and/or immunocytologically determined in breast cancer. (Hereinafter, the term immunohistochemical encompasses immunohistological as well as immunocytological). In all marker determinations, the skilled person must ensure that the test systems are capable of being qualitatively and quantitatively validated. Validation of some markers may be done using calibration against an internal or external standard and the generation of calibration curves through parallel measurement against positive and negative controls. However, generally these validation methods are very expensive and time consuming.

In immunohistochemistry, such a validation, especially a quantitative validation, is not trivial, because commercial kits for the immunohistochemical marker portrayal either contain no internal control at all or, for example as with the hormone receptor, contain cell preparations that are either positive or negative, i.e. only permit a yes/no decision and therefore can only be seen in the best case as a semi quantitative validation.

In an immunocytochemical staining kit HercpTest™ Code No. K 5204 market by DAKO, a control slide for validating a staining run for breast cancer is known. This control slide comprises three discrete and not mixed groups of cell line cells with known intensity score. By controlling if the groups of cell line cells give the pre-known results in a staining process, the staining process can be validated.

Thus, in practice, the trained pathologist carries out parallel determination of the marker to be examined on well characterized and pre-tested cases from his archive. This method is, on the one hand, technically uncertain or at least controversial as a result of the known heterogeneity of tissues and, on the other hand, ethically questionable, which makes a commercial realization of this procedure impossible.

Since the beginning of the 20th century, parameters for the determination of the proliferation activity have already been an integral component in the histopathological diagnosis of tumors. Immunohistologically, the portrayal of structures that controls the cell division cycle is used as markers for proliferation. Many of the participating cell cycle-associated proteins are transiently expressed in single cell cycle phases. In contrast to this, the nuclear Ki-67 protein (Gerdes, J., et al., Int. J. Cancer, 1983, 31: 13-20) is detectable in all active phases of the cell cycle, i.e. G1, S, G2 and mitosis, whereas resting phase cells (GO) are consistently negative for this protein (Gerdes, J., et al., J. Immunol., 1984,133: 1710-1715). This means that the Ki-67 protein expression (Ki-67 marker index) can serve as a measure for the growth fraction of a given cell population. For this, antibodies against the Ki-67 protein have found broad use in histopathology, especially in numerous studies on the use as a marker for malignancy assessment in human neoplasias (Sawhney, N. and Hall, P. A., J. Pathol, 1992, 168:161-162; Schwarting, R., Lab. Invest., 1993, 68:597-599; Lelle, R. J., et al., Cancer, 1987, 59:83-88; Lokhorst, H. M., et al., J. Clin. Invest, 1987, 79:1401-1411; Gerdes, J. et al., Am. J. Path., 1987 128:330-334 and 129:486-492).

In retrospective studies on various tumor entities, the role of the Ki-67 marker index as a prognosis marker is discussed in a different manner. While an unanimous correlation between the survival time of patients and the Ki-67 marker index was described for malignant non-Hodgkin's lymphomas (Gerdes, J. et al., 1987, Lancet, ii 448-449; Grogan, T. M. et al., 1988 Blood, 71:1157-1160; Hall, P. A. et al., J. Pathol. 1988, 154:223-235), this has been controversially discussed in part for breast cancer: Harberg et al. (Prognostic and relevant therapy factors in breast cancer, Novartis Pharma Publishers, Nürnberg, 1997) found no correlation in multi-variate analysis, whereas Querzoli, P. et. al., J. Clin. Pathol. 1996 November; 49(11):926-930; Veronese, S. M. et al., Anticancer Res. 1995 November; 15(6B):2717-2722; Clahsen, P. C. et al., J. Clin Oncol. 1998 February; 16(2):470-479; Rozan, S. et al., Int. J. Cancer 1998 February; 79(1): 27-33; Jansen, R. L. et al., Br. J. Cancer 1998 August; 78(4):460-465; Molino, A. et al., Int. J. Cancer 1997 August; 74(4):433-437; conclusively prove that the portrayal of the Ki-67 protein in paraffin sections with the monoclonal antibody MIB-1 in the multi-variate statistic analysis is an independent prognostic parameter in breast cancer. Aaltoma et al., 1997, Eur. Urol. 32: 410-415 and Borre et al., 1998, J. Urol. 159: 1609-1614, demonstrated that the Ki-67 marker index is also an independent prognostic parameter for prostate carcinoma, whereas Coetze et al., 1997, J. Urol. 157: 214-218, questioned the value of the Ki-67 marker index as a prognostic indicator, and Uzoaru et al., 1998, J. Surg. Oncol. 67: 33-37, even concluded that the Ki-67 marker index does not permit any significant prognosis for the survival of patients.

As demonstrated above by means of example on the hormone receptors, a standardization of immunostaining techniques as well as an internal validation of the quantitative analysis have not been possible up to now even with the promotion of the Ki-67 marker index.

SUMMARY OF THE INVENTION

Hence, an objective of the invention is to provide a tool for use in the qualitative and/or the quantitative validation of marker indices, especially in medical prognosis, diagnosis, such as immunohistochemical diagnosis, and especially for validation of a Ki-67 marker index, and determination of therapeutic relevance.

A further objective of the invention is to provide a tool for validation of marker indices, which tool is relatively fast and easy to use and can provide a reliable result.

Another objective of the invention is to provide a tool for validation of marker indices, which tool has a long durability from its production to its use.

These and other objectives are achieved by the invention as defined in the claims.

DETAILED DESCRIPTION OF THE INVENTION

The invention thus provides a tool designated as a pseudo-tissue. The pseudo-tissue according to the invention comprises two or more cell populations incorporated in a matrix.

The characterising feature of each of the cell populations is that it includes two or more cells which cells are substantially identical to each other with respect to the number of one or more specific marker(s), viz. the marker(s) of the marker indices which can be validated using the specific pseudo-tissue. The term "two or more cells, which are substantially identical to each other with respect to the number of a specific markers" means that the number of markers of the two or more cells preferably should not vary from each other more than about 20%, and preferably not more than 10%. The two or more cell populations shall differ from each other with respect to the one or more markers so that the cells from one population differ from the cells in another population of the pseudo-tissue with respect to the number of one or more of said specific marker(s). It is generally preferred that the number of the specific markers on the two or more cells in a cell populations should not vary more than 10% of the difference of the average number of markers on the cell in this population compared to the average number of the specific markers in another cell population in the pseudo tissue.

It is preferred that the cells from at least two cell populations are mixed with each other in the matrix, so that a pattern with points or areas having more or less markers is made. It is particularly preferred that the cells from at least two cell populations are mixed in a substantially homogeneous mixture to thereby provide a substantially homogeneous pattern of markers.

The marker or markers may in principle be any type of marker which can be detected by any means e.g. by using immunohistological, immunocytological, hybridization using immunofluorescence and/or immunoenzymatic, techniques. Such markers may be organic as well as inorganic substances e.g. selected from the group consisting of lipids, lipopolysaccharides, sugars, proteins, endogenous enzymes such as peroxidase or alkaline phosphatase, cell membrane structures with and without CD-characterization, cytoplasmic nucleotides and cytoplasmic nucleic acids. The markers particularly include any markers of diagnostic interest and especially proliferation markers such as Ki-67; hormone receptors such as estrogen receptors, progesterone receptors or androgen receptors; cytoskeleton compounds; hematological markers; oncogene products such as c-myc; cell membrane constituents; nuclear bound receptors; chromosomal aberrations such as gene amplifications, gene deletions, point mutations and translocations; and infectious agents.

As all the above described markers and their methods for detection are generally known in the art and will therefore not be described in further detail.

The cells in a cell population of the pseudo-tissue may be any type of cells, preferably eukaryotic cells grown in vivo or in vitro. The cells may be in any growth phase. Cell line cells, more preferably mixtures of two or more cell line cells, embedded in a matrix are understood as pseudo-tissues. Such pseudo-tissues should permit a histological, more preferably an immunohistological, examination.

It is preferred that the cells in at least one of the cell populations are culture cells which are cultured, collected and/or harvested in vitro. The cells may be transfected or transformed e.g. using isolated viral DNA genomes. The cells of a cell population may preferably be substantially equal to each other, and more preferably said substantially equal cells being of a single cell line.

To obtain a highly reliable determination using the pseudo tissue according to the invention the ratio of cells or markers in the respective cell population should be known.

Depending on the sensitivity of the marker detection, the ratio of cells from the two or more different cell populations in a pseudo-tissue may vary. In general, for most markers the preferred ratio of cells from two different cell populations are in the interval from $1:10^9$ to $10^9:1$, preferably in the interval from 1:20 to 20:1.

The material for the matrix may be any material which does not interfere with the markers or the detection of the markers and into which the cells can be incorporated in a matrix without thereby interfering with the markers or the detection of the markers. Furthermore it is preferred that the material for the matrix is dimensionally stable at 20° C., and that it is preferably possible to cut into fine sections of e.g. 50 nm and 100 µm. Preferably the material for the matrix is selected from the group consisting of plastics, paraffin and paraffin derivatives, agarose, non-heparinized serum, collagen, cellulose derivatives, chitin derivatives, chitosan derivatives, biopolymers, fibrin clots and mixtures thereof.

The pseudo-tissue may preferably be provided in the form of thin sections having a thickness of up to about 100 µm, more preferably between 50 nm and 100 µm, even more preferably sections between 80 and 120 nm or sections between 2 and 5 µm.

Prior to or after the incorporation of the cells into the matrix, the cells may preferably be fixed. Any common method of fixation of cells may in principle be used such as fixation performed using one or more fixatives selected from the group consisting of formalin, glutaraldehyde, osmium tetraoxide, acetic acid, ethanol, acetone, picric acid, chloroform, potassium dichromate and mercuric chloride and/or stabilizing using microwave heating or freezing. As it is generally known, the treatment with the fixative should be performed over sufficient time to stabilize the cells but still the time should preferably be kept sufficiently short so that the structure of the cells and the specific markers should be preserved.

The invention also relates to a diagnostic kit which comprises a pseudo-tissue for intra- and inter-assay standardization.

The diagnostic kit according to the invention for the quantification and qualification of a cell fraction comprising a marker, comprises a pseudo-tissue comprising two or more cell populations comprising cells which differ from one cell population to the other with respect to the number and/or reactivity effectiveness of one or more specific marker(s). Preferably the one or more cell populations are incorporated in a matrix as described above.

The diagnostic kit may preferably further comprise a component or a set of components for the detection of the marker or markers. The component for detection of the marker or markers naturally depends on the marker or markers to be detected, but for most diagnostic and prognostic purposes as well as for determining the therapeutic relevance the detection means include a component or set of components including one or more antibodies and/or active derivatives thereof, DNA or RNA probes, synthetic oligo-nucleotides, PNA, LNA, said component may preferably be linked to one or more enzymes and/or fluorescent compound, said set of components preferably being an enzyme and a reagent for the detection of an enzyme.

In a preferred embodiment of the invention the kit is a kit for detection and validation of a proliferation index, and the diagnostic kit includes a pseudo-tissue as defined above wherein the specific marker includes Ki-67 protein, and the component for the detection of the marker is an antibody directed against the Ki-67 protein, said antibody preferably being a member of the MIB® family, more preferably MIB®-1.

In a further preferred embodiment the diagnostic kit comprises antibodies against the Ki-67 protein with limited interspecies cross-reactivity, as well as fixed, paraffin-embedded pseudo-tissue comprising cell line mixtures with pre-defined marker indices, preferably Ki-67 marker index, or microscopic sections of pseudo-tissue as well as detection reagents.

The preferred diagnostic kit as defined above is particularly suitable for the validation of the Ki-67 marker index. As it is clear for a skilled person, however, the kit and the pseudo-tissue may be varied in many ways. By using positive and negative hormone receptor cell line cells for the production of a pseudo-tissue for use in a corresponding kit, the invention is also useable for the validation of the immunohistochemical determination of the receptor status. By analogy, this is also true for the determination of the HER-2/neu (c-erb-B2) gene and protein expression in breast cancer. By using CD4 positive, CD8 negative and CD4 negative, CD8 positive cell line cells for the production of a pseudo-tissue for use in the corresponding kit, the invention is also suitable for the validation of the determination of the T4/T8 quotient. Consequently, the present invention is capable of being used for the validation of most varied marker indices.

The diagnostic kit according to the invention may preferably comprise two or more pseudo-tissues as defined above, wherein the two or more pseudo-tissues have different marker indices for one or more of the specific markers defined as the number of marker-positive cells for said specific marker in percent. By including two or more pseudo-tissues in a kit an even more reliable validation may be obtained.

The invention further relates to an analytic method for qualitative and/or quantitative determination of marker indices of a cell fraction labeled by said marker for in vitro diagnosis. The method includes the use of a pseudo-tissue according to the invention and may preferably include the use of the diagnostic kit according to the invention. The method comprises the steps of:
  i) providing a pseudo-tissue of Applicant's invention, wherein the pseudo-tissue has a predetermined quality and/or quantity of markers,
  ii) subjecting the cell fraction and the pseudo-tissue to a component or a set of components for the detection of the marker reactions;
  iii) determining the quality and/or quantity of markers of the cell fraction by using the detected marker reactions of the pseudo-tissue.

The pseudo-tissue of Applicant's invention includes a pseudo-tissue comprising two or more cell populations incorporated in a matrix, said cell populations each includes two or more cells which cells being substantially identical to each other with respect to the number of one or more specific marker(s), and said two or more cell populations comprising cells which differ from one cell population to the other with respect to the number of one or more of said specific marker(s), said cells from at least two cell populations preferably being mixed with each other in the matrix, more preferably mixed in a substantially homogeneous mixture.

The pseudo-tissue comprises one or more markers selected from the group consisting of lipids, lipopolysaccharides, sugars, proteins, cell membrane structures with and without CD-characterization, cytoplasmic nucleotides and nucleic acids, wherein the markers of the pseudo-tissue are detectable, preferably by using immunohistological, immunocytological, hybridization using immunofluorescence and/or immunoenzymatic techniques; and one or more markers are selected from the group consisting of proliferation markers such as Ki-67; hormone receptors such as estrogen receptors, progesterone receptors or androgen receptors; cytoskeleton compounds; hematological markers; oncogene products such as c-myc; cell membrane constituents; nuclear bound receptors; chromosomal aberrations such as gene amplifications, gene deletions, point mutations and translocations; and infectious agents.

The pseudo-tissue comprises cells in at least one of the cell populations being culture cells being cultured, collected and/or harvested in vitro, the cells of at least one cell population optionally being transfected and the cells of a cell population preferably being substantially equal to each other, and more preferably said substantially equal cells being of a single cell line.

The pseudo tissue comprises cells of two or more cell populations wherein ratio of cells from two different cell populations is in the interval from $1:10^9$ to $10^9:1$, preferably in the interval from 1:20 to 20:1.

The pseudo-tissue comprises a matrix selected from the group consisting of plastics, paraffin and paraffin derivatives, agarose, non-heparinized serum, collagen, cellulose derivatives, chitin. derivatives, chitosan derivatives and mixtures thereof.

The pseudo-tissue comprises cells of one or more cell populations that have been fixed or stabilized prior to or after incorporation in the matrix, the fixation/stabilization preferably being performed using one or more fixatives selected from the group consisting of formalin glutaraldehyde, osmium tetraoxide, acetic acid, ethanol, acetone, picric acid, chloroform, potassium dichromate and mercuric chloride and/or stabilizing by microwave heating or freezing.

The analytic method according to the invention may include the qualitative and/or quantitative determination of one or more additional markers, wherein the one or more additional markers are determined by using one or more pseudo tissues comprising at least one cell population having different marker indices for said one or more further markers.

Using the analytic method, of the invention, each detection series for the portrayal of a marker with the aid of a kit according to the invention includes the portrayal of the marker in the matching pseudo-tissue. Thus, the trained pathologist can qualitatively judge the portrayal of the marker (did the reaction turn out satisfactorily) as well as quantitatively validate the portrayal of the marker (was the pre-defined marker index in this detection series attained, and is therefore valid, or is the detection invalid by falling short or exceeding the pre-defined deviation threshold of the pre-defined marker index, as a rule plus/minus a standard deviation).

According to the invention, tissue samples, cytopreparations and cell/blood smears are included as material to be examined by using the analytic method.

Marker indices are in part differentially promoted. As mentioned above, the relationship of CD4 positive to CD8 positive cells is portrayed as the so-called T4/T8 quotient in the diagnosis of AIDS. However, generally marker index means the number of marker-positive cells of a certain population in percent. The latter definition is also valid for the Ki-67 marker index.

Also the invention relates to the method for the production of a pseudo-tissue comprising the steps of
 i) selecting a first cell population comprising cells which cells is substantially identical to each other with respect to the number of one or more specific marker(s) as defined above;
 ii) selecting a second population comprising cells which cells is substantially identical to each other with respect to the number of said one or more specific marker(s) as defined above, the cells of the second cell populations differ from the cells of said first cell population with respect to the number of one or more of said specific marker(s)as described above,
 iii) incorporating the first and the second cell population into a matrix as defined above.

The numbers of cells in the cell populations are as defined above. Prior to or after the incorporation into the matrix, the cells may preferably be fixed as described above.

The matrix with the cells may initially be provided in the form of a lump, e.g. a tube formed lump, which lump subsequently is cut into sections preferably having a thickness of up to about 100 μm, more preferably between 50 nm and 100 μm, even more preferably thin sections between 80 and 120 nm or thick sections between 2 and 5 μm. The desired thickness of the sections depends largely on the method of detection desired to be used, and the skilled person will easily be able to find the optimal thickness for a specific detection method.

As also claimed, the diagnostic kit and the pseudo-tissue of the invention may be used for the quantitative and/or qualitative measaure of one or more marker(s) in a sample, for the determination of the proliferation index and in a preferred embodiment for in vitro diagnosis in the diagnosis and treatment of cancer.

EXAMPLES

Figure 1:
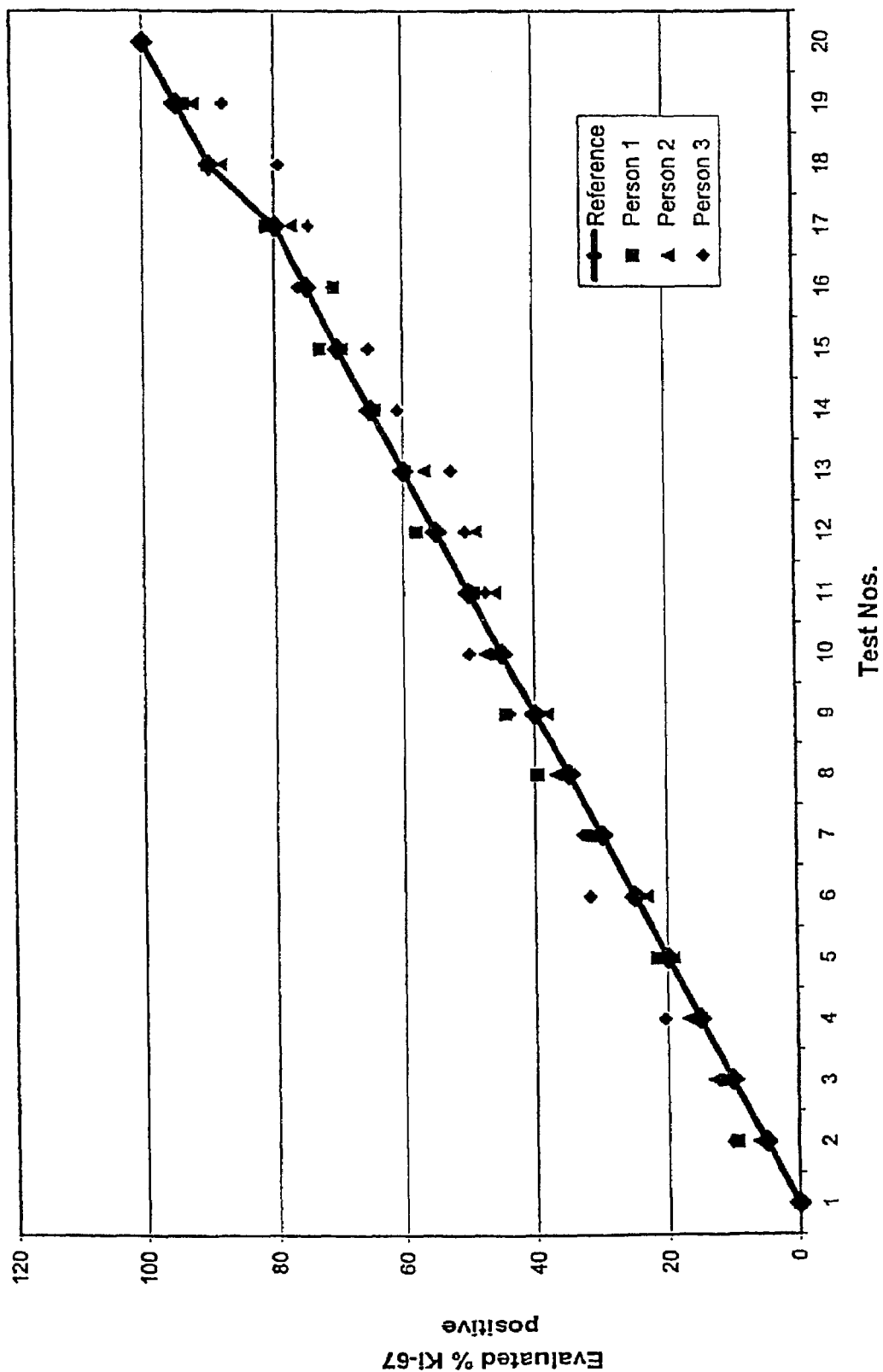
FIG. 1: intra-observer variability, series 1

The invention is more closely illustrated in the following by means of a preferred embodiment, but it is not limited in any way by this.

Some antibodies against the human Ki-67 protein demonstrate a limited cross-reaction with the Ki-67 proteins of other species. Thus, the monoclonal antibody MIB-1, for example, is excellently suited for the portrayal of the human Ki-67 protein in paraffin sections. However, the detection of murine equivalents on paraffin sections cannot be successfully performed with the antibody MIB-1. This limited inter-species cross-reactivity is used in the preparation of pseudo-tissues with pre-defined Ki-67 marker index.

Production of the Pseudo-Tissue

A human cell line, preferably IM-9, and a non-human, preferably murine, cell line, particularly preferred Ag8, are seeded under standard conditions and harvested in the logarithmic growth phase and dead cells and cell detritus are separated by means of density centrifugation. After a single wash in culture medium, the cell number is determined with a Sysmex Platelet Counter PL-100 (Sysmex TOA Medical Elektronics GmBH, Tarpen 15 A, D-22419, Hamburg). For this, 10 μl cell suspension is mixed well in 5 ml buffer (Sysmex Cellpack PK—30 L 20 liter, order number 834-0011-6) and the counting is carried out as a double determination. (Setting of the counter: discrimmator: blood 10, platelet 6; sensitivity: 1; alarm time: 11). Based on this counting, $1 \times 10^7$ cells are used for the production of the pseudo-tissue.

Reagents used: fibrinogen: F 4753, Sigma; batch: 60 mg in a test beaker and slowly add 10 ml 0.9% NaCl solution. Leave standing for 10 min at 37° C., thereafter it is resuspended with a pipette until the solution is clear. The solution prepared in this manner is stable for 24 hours.

Thrombin: T 9010, Sigma; batch: dissolve 1 vial in 500 μl tri-distilled water, resuspend well. Aliquots that are stored in solution at −20° C. are stable for 6 months. Centrifuge $1 \times 10^7$ cells in 1.5 ml screw tube at 1200 rpm, decant the supernatant. Resuspend the pellet (approx. 500-100 μl) well. Add 200 μl of the fibrinogen solution to the cells and resuspend well. Then, add 100 μl of the thrombin solution to this, mix briefly and incubate on ice for 30 min. When doing this, a fibrin clot including the cells forms which, in a routine manner, is subsequently fixed by formalin and is embedded in paraffin (4% formalin, at least 30 min., max. 60 hours; performance of the embedding in paraffin in a commercially available automated machine, for example Hypercenter™ of the company Shandon.) The paraffin sections produced by standard methods were then immunocytochemically stained as in the examples.

As portrayed in example 1, paraffin sections of pseudo-tissues of the murine cell line Ag8 were completely negative for MIB-1 as expected. Paraffin sections of pseudo-tissues of the human cell line IM9, prepared as described above, were almost 100% positive for MIB-1. This means that, by simple mixing of these cell lines at different percentages, pseudo-tissues must be able to be prepared with every desired percentage of MIB-1 positive cells. Example 2 demonstrates that this is the case. By using the pseudo-tissue preparations in a MIB-1 detection kit™ for the control of the determination of the growth fraction with antibodies against the human Ki-67 protein, a qualitative as well as quantitative internal validation of this determination has become possible for the first time.

Example 1

MIB-1 immunostaining of pseudo-tissues whose cells consist of 100% of IM9 or Ag8 cell line cells.

1-3 μm thick sections were stained with the following reagents of the company Monotec, Hamburg, according to the following formula.

Reagents of the MIB-1 Detection Kit

Staining Instructions

De-Paraffination and Rehydration

Before immunostaining, the paraffin sections applied to the slide must be de-paraffinated in order to remove the embedding medium. Subsequently, the sections must be rehydrated. Insufficient de-parafination and insufficient rehydration are to be avoided by all means, because this can lead to an increased non-specific staining and decreased specific staining.

| Vial | Amount | Description |
|---|---|---|
| 1 | 1 × 10 ml | Peroxidase blocking reagent |
| 2 | 1 × 5 ml | Mouse monoclonal antibody MIB-1: ready-to-use antibody purified from culture supernatant in PBS (0.01 M sodium phosphate, 0.25 M NaCl, pH 7.4-7.6) with stabilizing protein and sodium azide) Immunogen: bacterially expressed portions of exon 13 of the human Ki-67 CDNA Clone: MIB-1 Subclass: IgG 1 kappa Total protein concentration: 2.0 g/l Specific IgG: 1 µg/ml Concentration of irrelevant antibodies: 0.0 mg/ml Specificity: human Ki-67 protein Preparation method: cell culture Purification method: protein A chromatography |
| 3 | 1 × 10 ml | Detection reagent: peroxidase-conjugated affinity chromatography-purified goat anti-mouse IgG (minimized cross-reaction with human, bovine and horse serumproteins) in PBS with stabilizing protein and an anti-microbial agent. |
| 4 | 1 × 5 ml | Negative control reagent: immunoglobulin fraction from normal mouse serum at equivalent protein concentration as with the antibody MIB-1. In PBS with stabilizing protein and sodium azide. |
| 5 | 1 × 10 ml | DAB substrate: substrate buffer solution, pH 7.4-7.8, with $H_2O_2$, stabilizer and anti-microbial agent. |
| 6 | 1 × 0.5 ml | DAB chromogen: 3,3'-diaminobenzidine as a concentrate in solvents and stabilizers. |
| 7 | 1 × 50 ml | Antigen recovery solution (×50): citrate buffer with anti-microbial agent. |
| 8 | 1 × 100 ml | Wash buffer (×30): Tris/HCl buffered saline, pH 7.4-7.6, with anti-microbial agent. |

Step 1: sections are incubated in a xylene bath for 5 (+/−1) minutes. A change of bath and incubation is repeated once.

Step 2: allow the excess liquid to run off and then incubate the sections in a 100% alcohol bath for 5 (+/−1) minutes. A change of bath and incubation is repeated once.

Step 3: allow the excess liquid to run off and then incubate the sections in a 70% alcohol bath for 5 (+/−1) minutes. A change of bath and incubation is repeated once.

Step 4: allow the excess liquid to run off and then incubate the sections in a 40% alcohol bath for 5 (+/−1) minutes. A change of bath and incubation is repeated once.

Step 5: allow the excess liquid to run off and then incubate the sections in a distilled water bath for 5 (+/−1) minutes. A change of bath and incubation is repeated once.

The xylene, alcohol and water baths must each be changed after 40 sections.

Immunostaining Protocol:

Step 1: Peroxidase Blocking Agent

Allow the excess distilled water to run off well. Thoroughly and carefully dry around the slide with a non-linting cloth in order to ensure that the reagents cover the section. Then place the sections in a moist chamber and bring 100 µl of peroxidase blocking agent (vial 1) onto the section. (If necessary, more than 100 µl must be applied).

Incubate for 10(+/−1) minutes at room temperature.

Then, carefully rinse the sections with distilled water or wash buffer with the aid of a wash bottle, whereby it is to be taken care that the jet of liquid does not touch the section.

Step 2: Antigen Recovery

Place the slide cuvet in a water bath and fill it with antigen recovery solution (vial 7) diluted 1:50 in distilled water. Heat the water bath, and therewith the antigen recovery solution, to 95-99° C. Subsequently, place the peroxidase-blocked sections in these cuvets and bring the temperature to 95-99° C. again and then incubate for 60(+/−1) minutes at 95-99° C.

Take the slide cuvet out of the warm water bath and transfer the sections into a fresh wash buffer at room temperature, incubate for 3(+/−1) minutes, then repeat the wash buffer change and wash cycle twice.

Step 3: Primary Antibody MIB-1 and/or the Negative Control Reagent

Allow the excess wash buffer to run off and dry around the section as described above.

Cover the sections with 100 µl of primary antibody from vial 2 or cover sections with 100 µl of negative control reagent from vial 4.

Incubate for 30(+/−1) minutes at room temperature.

Then, carefully rinse the sections with distilled water or wash buffer with the aid of a wash bottle, whereby it is to be taken care that the jet of liquid does not touch the section, and transfer the sections into a fresh wash buffer, incubate for 3(+/−1) minutes, then repeat the wash buffer change and wash cycle twice as in step 2.

Step 4: Detection Reagent

Allow the excess wash buffer to run off and dry around the section as described above.

Cover the sections with 100 µl of detection reagent from vial 3.

Incubate for 30(+/−1) minutes at room temperature.

Then, carefully rinse the sections with distilled water or wash buffer with the aid of a wash bottle, whereby it is to be taken care that the jet of liquid does not touch the section and transfer the sections into a fresh wash buffer, incubate for 3(+/−1) minutes, then repeat the wash buffer change and wash cycle twice as in step 2.

Step 5: Development Reaction

Allow the excess wash buffer to run off and dry around the section as described above.

Add 1 ml DAB substrate from vial 5 into the reagent glass and add 10 µl DAB chromogen to this. Add 100 µl of this solution to the sections.

Incubate for 10(+/−1) minutes at room temperature.

Subsequently, wash as described above.

Counter-stain with Mayer's hematoxylin and then cover in Kaiser's glycerin gelatin (embedding media such as Faramount® or Depex®).

The evaluation of the staining occurs microscopically by the counting of 200 cells each by 3 different people and determining the percentage of the positive cells in the stained material.

Ad AG8-Pseudo-Tissue

All stainings with the negative control reagent as well as with the MIB-1 antibody were negative, i.e. 0% positive cells were present. Intra- as well as inter-assay deviation as well as intra- and inter-observer deviations were equal to 0.

Ad IM9-Pseudo-Tissue

All stainings with the negative control reagent were negative as expected. 0% positive cells.

Intra- as well as inter-assay deviation as well as intra- and inter-observer deviations for the negative control reagent were equal to 0.

MIB-1 stained sections of the IM9-pseudo-tissue almost always demonstrated 100% positive cells (average value 99.833%). In the test series depicted in table 1a and 1b, the intra- and inter-observer as well as the inter-assay deviations were very small.

Example 2

Immunostaining of pseudo-tissues with defined amounts of AG8 and IM9 cells.

As depicted above, paraffin blocks of pseudo-tissues were produced with defined amounts of AG8 and/or IM9 cells, respectively, (0, 5, 10, 15, 20, 25, 30, 35, 40, 45, 50, 55, 60, 65, 70, 75, 80, 85, 90, 95 and 100%).

Paraffin sections were then immunostained as depicted in example 1.

All stainings with the negative control reagent were negative for all blocks as expected. 0% positive cells. Intra- as well as inter-assay deviation as well as intra- and inter-observer deviations for the negative control reagent were equal to 0.

Two series were performed.

Figure 2:
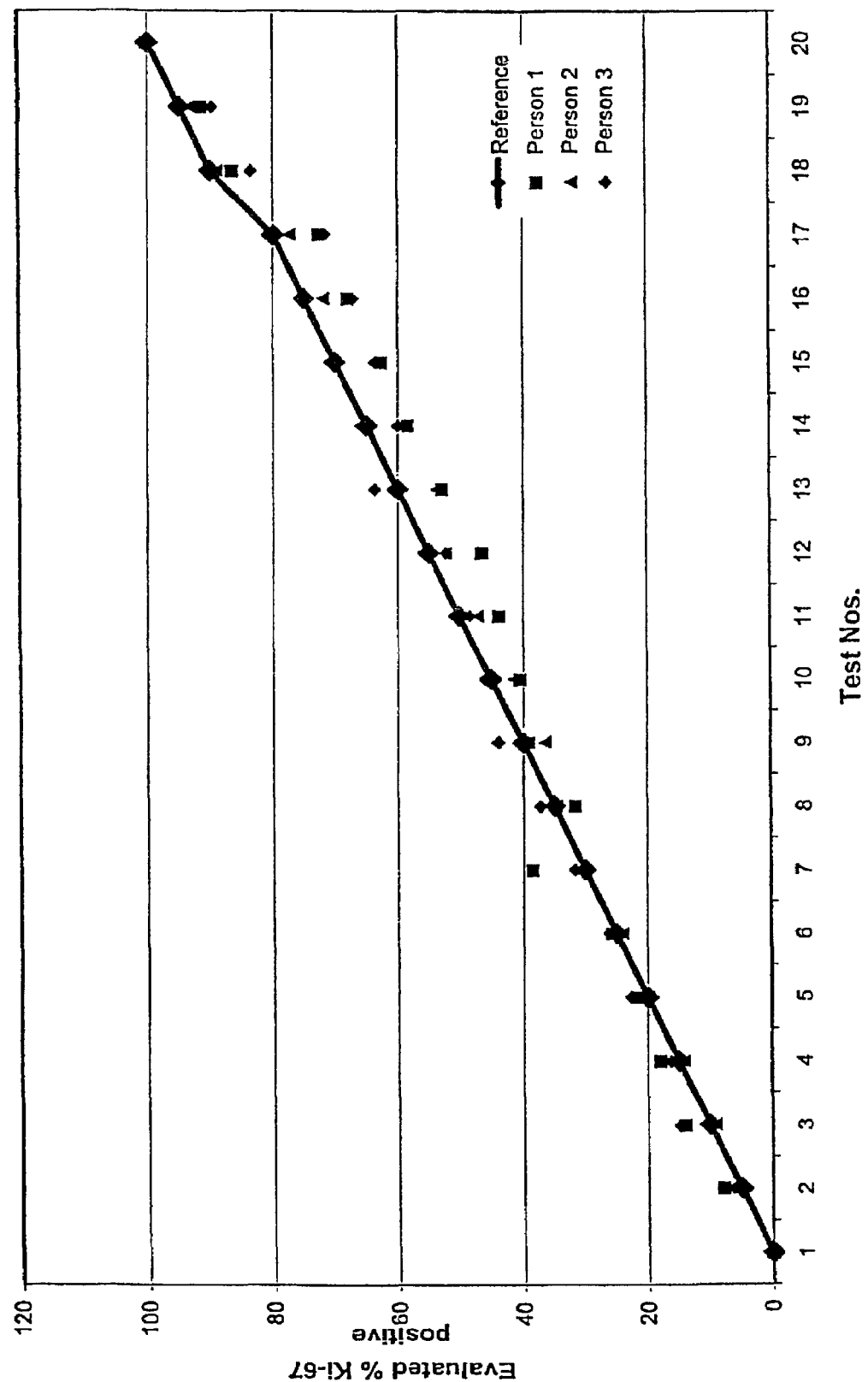
FIG. 2: inter-observer variability, series 2

The results for the MIB-1 The intra-observer stainings for the two series are summarized in table 1a and 1b and shown in FIGS. 1 and 2, respectively. As it can be observed all raised values are very close to the reference and thereby within the confidence interval.

Figure 3:
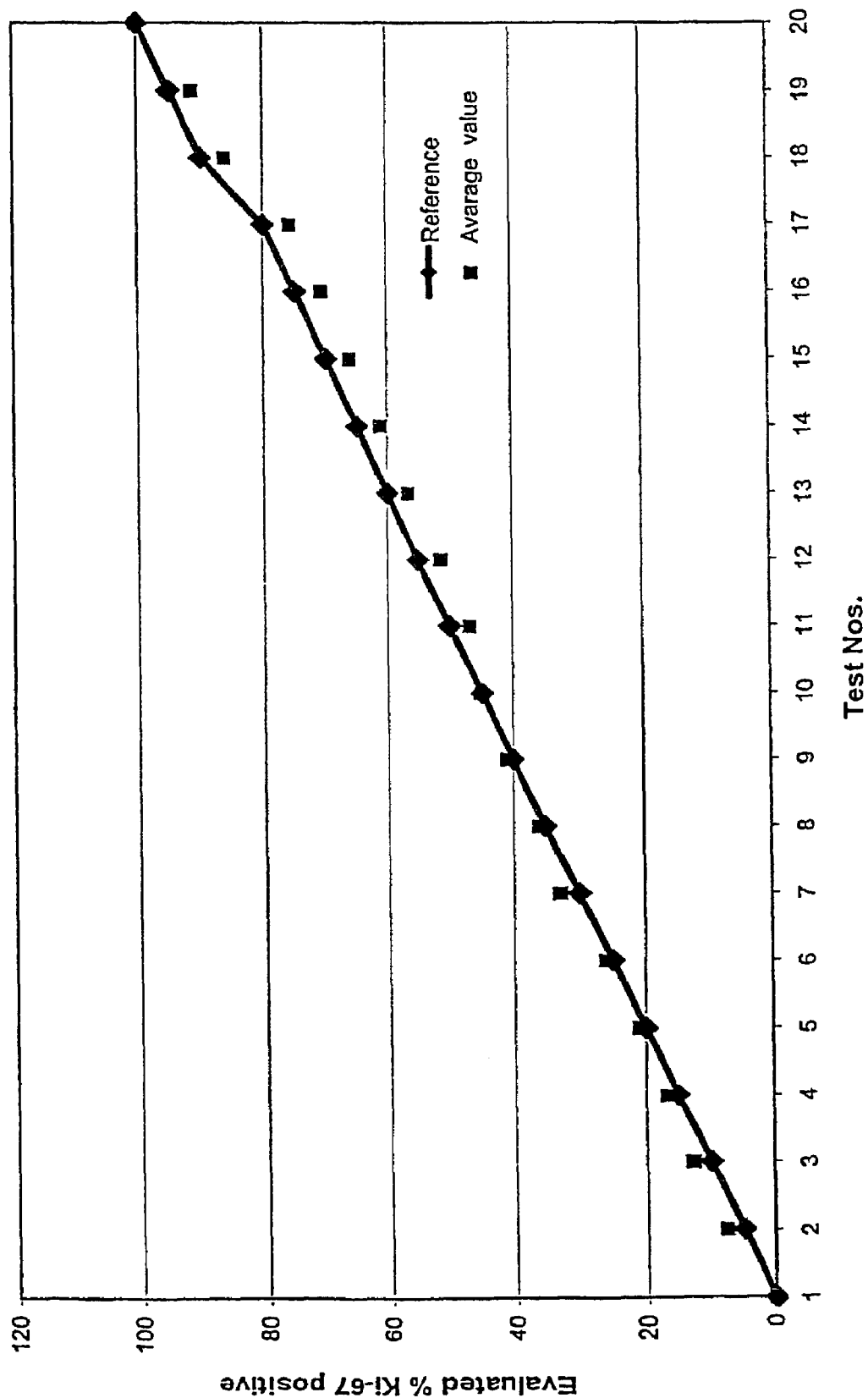
FIG. 3: inter-assay variability

In table two the average value of the intra-observer test is calculated and the result is shown in FIG. 3 as the inter-assay variability.

TABLE 1a

| | | Series 1 | | | | | | | | | | | |
|---|---|---|---|---|---|---|---|---|---|---|---|---|---|
| | | Person 1 | | | | Person 2 | | | | Person 3 | | | |
| Set point | Refe-rence | #1 | #2 | #3 | Average value | #1 | #2 | #3 | Average value | #1 | #2 | #3 | Average value | Average value Series 1 |
| 0 | 0 | 0 | 0 | 0 | 0.0 | 0 | 0 | 0 | 0.0 | 0 | 0 | 0 | 0.0 | 0.0 |
| 5 | 5 | 8 | 13.5 | 6.5 | 9.3 | 6 | 7.5 | 4.5 | 6.0 | 11 | 10 | 9 | 10.0 | 8.4 |
| 10 | 10 | 12 | 10.5 | 11.5 | 11.3 | 13 | 12.5 | 13 | 12.8 | 13.5 | 15.5 | 13.5 | 14.2 | 12.8 |
| 15 | 15 | 15.5 | 17 | 12 | 14.8 | 16 | 18 | 16.5 | 16.8 | 18 | 30.5 | 13 | 20.5 | 17.4 |
| 20 | 20 | 24 | 18 | 23 | 21.7 | 20 | 16 | 21.5 | 19.2 | 18 | 21.5 | 22 | 20.5 | 20.4 |
| 25 | 25 | 28.5 | 21 | 25.5 | 25.0 | 23 | 24 | 23 | 23.3 | 37.5 | 26 | 32 | 31.8 | 26.7 |
| 30 | 30 | 34.5 | 27 | 33 | 31.5 | 29.5 | 31.5 | 33 | 31.3 | 37 | 27 | 34.5 | 32.8 | 31.9 |
| 35 | 35 | 41.5 | 41 | 36.5 | 39.7 | 40 | 35 | 36 | 37.0 | 32.5 | 37 | 33 | 34.2 | 36.9 |
| 40 | 40 | 43.5 | 43.6 | 46 | 44.4 | 43 | 31 | 41 | 38.3 | 43 | 46 | 42.5 | 43.8 | 42.2 |
| 45 | 45 | 49.5 | 44.5 | 43.5 | 45.8 | 52 | 42 | 49 | 47.7 | 52.5 | 54.5 | 43 | 50.0 | 47.8 |
| 50 | 50 | 48 | 52.5 | 47.5 | 49.3 | 47 | 47 | 44 | 46.0 | 44.5 | 52.5 | 45.5 | 47.5 | 47.6 |
| 55 | 55 | 55 | 60 | 58.5 | 57.8 | 50 | 48 | 49 | 49.0 | 49.5 | 49.5 | 52.5 | 50.5 | 52.4 |
| 60 | 60 | 64.5 | 49 | 65.5 | 59.7 | 57 | 62 | 51 | 56.7 | 46 | 56 | 56 | 52.7 | 56.3 |
| 65 | 65 | 61 | 64 | 68 | 64.3 | 62 | 65 | 68 | 65.0 | 69 | 59 | 54.5 | 60.8 | 63.4 |
| 70 | 70 | 69 | 71.5 | 78 | 72.8 | 71 | 71 | 66 | 69.3 | 60 | 68.5 | 67.5 | 65.3 | 69.2 |
| 75 | 75 | 61.5 | 74 | 76 | 70.5 | 69.5 | 68 | 75 | 70.8 | 70 | 67.5 | 91.5 | 76.3 | 72.6 |
| 80 | 80 | 77 | 84 | 82.5 | 81.2 | 76.5 | 79.5 | 76 | 77.3 | 80.5 | 75 | 68.5 | 74.7 | 77.7 |
| 90 | 90 | 91.5 | 88 | 91 | 90.2 | 87 | 89 | 88 | 88.0 | 83 | 74 | 81 | 79.3 | 85.8 |
| 95 | 95 | 92.5 | 94 | 95 | 93.8 | 89.5 | 94 | 94 | 92.5 | 92 | 84 | 87.5 | 87.8 | 91.4 |
| 100 | 100 | 100 | 100 | 100 | 100.0 | 100 | 100 | 100 | 100.0 | 100 | 100 | 100 | 100.0 | 100.0 |

TABLE 1b

| | | Series 2 | | | | | | | | | | | |
|---|---|---|---|---|---|---|---|---|---|---|---|---|---|
| | | Person 1 | | | | Person 2 | | | | Person 3 | | | |
| Set point | Refe-rence | #1 | #2 | #3 | Average value | #1 | #2 | #3 | Average value | #1 | #2 | #3 | Average value | Average value Series 2 |
| 0 | 0 | 0.0 | 0.0 | 0.0 | 0.0 | 0.0 | 0.0 | 0.0 | 0.0 | 0.0 | 0.0 | 0.0 | 0.0 | 0.0 |
| 5 | 5 | 5.0 | 12.0 | 6.5 | 7.8 | 7.0 | 6.0 | 6.0 | 6.3 | 6.0 | 5.0 | 7.5 | 6.2 | 6.8 |
| 10 | 10 | 16.0 | 16.0 | 10.0 | 14.0 | 9.0 | 9.0 | 9.5 | 9.2 | 13.0 | 15.5 | 16.0 | 14.8 | 12.7 |
| 15 | 15 | 15.5 | 23.0 | 15.5 | 18.0 | 14.0 | 12.5 | 16.0 | 14.2 | 16.5 | 17.5 | 15.0 | 16.3 | 16.2 |
| 20 | 20 | 22.5 | 23.0 | 18.5 | 21.3 | 20.0 | 19.0 | 21.0 | 20.0 | 26.0 | 20.5 | 21.5 | 22.7 | 21.3 |
| 25 | 25 | 25.5 | 27.0 | 24.5 | 25.7 | 22.0 | 25.5 | 24.5 | 24.0 | 25.0 | 32.0 | 21.5 | 26.2 | 25.3 |
| 30 | 30 | 32.5 | 48.0 | 35.0 | 38.5 | 32.5 | 31.0 | 29.5 | 31.0 | 30.0 | 30.5 | 34.5 | 31.7 | 33.7 |
| 35 | 35 | 28.5 | 32.0 | 34.5 | 31.7 | 35.5 | 37.0 | 31.5 | 34.7 | 38.0 | 37.5 | 36.5 | 37.3 | 34.6 |
| 40 | 40 | 38.5 | 37.5 | 41.5 | 39.2 | 38.0 | 34.5 | 37.0 | 36.5 | 44.0 | 43.5 | 44.0 | 43.8 | 39.8 |
| 45 | 45 | 35.0 | 43.5 | 43.0 | 40.5 | 45.0 | 38.0 | 41.0 | 41.3 | 46.0 | 39.5 | 52.0 | 45.8 | 42.6 |
| 50 | 50 | 39.5 | 44.0 | 47.5 | 43.7 | 46.0 | 46.0 | 49.0 | 47.0 | 50.0 | 50.5 | 44.5 | 48.3 | 46.3 |
| 55 | 55 | 42.0 | 47.0 | 50.0 | 46.3 | 58.0 | 48.5 | 50.0 | 52.2 | 46.5 | 57.5 | 52.5 | 52.2 | 50.2 |
| 60 | 60 | 51.5 | 55.0 | 51.5 | 52.7 | 56.5 | 50.0 | 54.0 | 53.5 | 86.0 | 49.5 | 55.5 | 63.7 | 56.6 |
| 65 | 65 | 57.0 | 61.0 | 57.0 | 58.3 | 60.0 | 53.0 | 62.5 | 58.5 | 59.5 | 62.0 | 58.5 | 60.0 | 58.9 |
| 70 | 70 | 62.5 | 62.0 | 63.5 | 62.7 | 64.0 | 66.0 | 60.0 | 63.3 | 67.0 | 64.5 | 59.5 | 63.7 | 63.2 |
| 75 | 75 | 51.5 | 66.0 | 86.0 | 67.8 | 71.0 | 70.0 | 74.5 | 71.8 | 67.0 | 65.0 | 69.5 | 67.2 | 68.9 |
| 80 | 80 | 69.5 | 77.0 | 71.0 | 72.5 | 76.5 | 78.0 | 77.5 | 77.3 | 76.5 | 68.0 | 70.5 | 71.7 | 73.8 |
| 90 | 90 | 84.5 | 90.0 | 85.0 | 86.5 | 89.0 | 89.5 | 88.0 | 88.8 | 84.5 | 82.5 | 83.5 | 83.5 | 86.3 |
| 95 | 95 | 88.5 | 90.0 | 96.0 | 91.5 | 95.0 | 92.0 | 93.0 | 93.3 | 89.0 | 91.0 | 89.5 | 89.8 | 91.6 |
| 100 | 100 | 100.0 | 100.0 | 100.0 | 100.0 | 100.0 | 100.0 | 100.0 | 100.0 | 100.0 | 100.0 | 100.0 | 100.0 | 100.0 |

TABLE 2

| | | | Series 1 and 2 | | | |
|---|---|---|---|---|---|---|
| Average value Series 1 Person 1 | Average value Series 1 Person 2 | Average value Series 1 Person 3 | Average value Series 2 Person 1 | Average value Series 2 Person 2 | Average value Series 2 Person 3 | Average value Series 1 + 2 |
| 0.0 | 0.0 | 0.0 | 0.0 | 0.0 | 0.0 | 0 |
| 9.3 | 6.0 | 10.0 | 7.8 | 6.3 | 6.2 | 7.6 |
| 11.3 | 12.8 | 14.2 | 14.0 | 9.2 | 14.8 | 12.7 |
| 14.8 | 16.8 | 20.5 | 18.0 | 14.2 | 16.3 | 16.8 |
| 21.7 | 19.2 | 20.5 | 21.3 | 20.0 | 22.7 | 20.9 |
| 25.0 | 23.3 | 31.8 | 25.7 | 24.0 | 26.2 | 26.0 |
| 31.5 | 31.3 | 32.8 | 38.5 | 31.0 | 31.7 | 32.8 |
| 39.7 | 37.0 | 34.2 | 31.7 | 34.7 | 37.3 | 35.8 |
| 44.4 | 38.3 | 43.8 | 39.2 | 36.5 | 43.8 | 41.0 |
| 45.8 | 47.7 | 50.0 | 40.5 | 41.3 | 45.8 | 45.2 |
| 49.3 | 46.0 | 47.5 | 43.7 | 47.0 | 48.3 | 47.0 |
| 57.8 | 49.0 | 50.5 | 46.3 | 52.2 | 52.2 | 51.3 |
| 59.7 | 56.7 | 52.7 | 52.7 | 53.5 | 63.7 | 56.5 |
| 64.3 | 65.0 | 60.8 | 58.3 | 58.5 | 60.0 | 61.2 |
| 72.8 | 69.3 | 65.3 | 62.7 | 63.3 | 63.7 | 66.2 |
| 70.5 | 70.8 | 76.3 | 67.8 | 71.8 | 67.2 | 70.7 |
| 81.2 | 77.3 | 74.7 | 72.5 | 77.3 | 71.7 | 75.8 |
| 90.2 | 88.0 | 79.3 | 86.5 | 88.8 | 83.5 | 86.1 |
| 93.8 | 92.5 | 87.8 | 91.5 | 93.3 | 89.8 | 91.5 |
| 100.0 | 100.0 | 100.0 | 100.0 | 100.0 | 100.0 | 100.0 |

Example 3

Immunostaining of Pseudo-Tissues

Pseudo-tissues each with a 50% amount of the cell lines Raji (human) and Ag8 (murine) or Jurkat and Ag8 were also produced. The results of MIB-1 staining of sections of these pseudo-tissues were in the same range as portrayed in example 2 for the 50% pseudo-tissue of IM9 and Ag8. Thus, the pseudo-tissue can also be reliably prepared with other cell line cell combinations.

The invention claimed is:

1. A pseudo-tissue for the qualitative and quantitative validation of marker indices comprising a substantially homogeneous mixture of at least two different isolated cell populations fixed prior to incorporation in a matrix, wherein each said cell population comprises two or more cells that are substantially identical to each other with respect to the number of one or more specific marker(s), and said cell populations differ from each other with respect to the number of said one or more specific marker(s); and wherein the ratio between the cells of at least one of the cell populations and the cells of at least one different cell population is known.

2. The pseudo-tissue of claim 1, wherein the marker is detectable by using an immunohistological, an immunocytological, and a hybridization technique.

3. The pseudo-tissue of claim 2, wherein the immunohistological, the immunocytological, and the hybridization technique is an immunofluorescence technique.

4. The pseudo-tissue of claim 2, wherein the immunohistological, the immunocytological, and the hybridization technique is an immunoenzymatic technique.

5. The pseudo-tissue of claim 1, wherein the marker is a proliferation marker.

6. The pseudo-tissue of claim 5, wherein the proliferation marker is Ki-67.

7. The pseudo-tissue of claim 1, wherein the marker is a hormone receptor.

8. The pseudo-tissue of claim 7, wherein the hormone receptor is selected from the group consisting of an estrogen receptor, a progesterone receptor and an androgen receptor.

9. The pseudo-tissue of claim 1, wherein the marker is an oncogene product.

10. The pseudo-tissue of claim 9, wherein the oncogene product is c-myc.

11. The pseudo-tissue of claim 1, wherein the marker is a chromosomal aberration.

12. The pseudo-tissue of claim 11, wherein the chromosomal aberration is selected from the group consisting of a gene amplification, a gene deletion, a point mutation and a translocation.

13. The pseudo-tissue of claim 1, wherein the cells in at least one of the at least two cell populations are cells that have been cultured, collected and/or harvested in vitro.

14. The pseudo-tissue of claim 13, wherein said cells of at least one of the cell populations are transfected.

15. The pseudo-tissue of claim 13, wherein said cells of at least one of the cell populations are substantially identical to each other with respect to the number of one or more specific marker(s).

16. The pseudo-tissue of claim 15, wherein said substantially identical cells are of a single cell line.

17. The pseudo-tissue of claim 1, wherein a ratio between cells of the at least one cell population and the cells of the at least one different cell population in the substantially homogenous cell mixture is from $1:10^9$ to $10^9:1$.

18. The pseudo-tissue of claim 1, wherein a ratio between cells of the first cell population and cells of the second cell population in the substantially homogenous cell mixture is from 1:20 to 20:1.

19. The pseudo-tissue of claim 1, wherein the matrix is selected from the group consisting of a plastic, a paraffin, a paraffin derivative, an agarose, a non-heparinized serum, a collagen, a cellulose derivative, a chitin derivative, and a chitosan derivative.

20. The pseudo-tissue tissue of claim 1, wherein said fixation is performed using one or more fixatives selected from the group consisting of a formalin, a glutaraldehyde, an osmium tetraoxide, an acetic acid, an ethanol, an acetone, a picric acid, a chloroform, a potassium dichromate and a mercuric chloride fixative.

21. The pseudo-tissue of claim 1, wherein at least one of the one or more specific markers is a marker for intra- and inter-assay standardization.

22. The pseudo-tissue of claim 1, wherein at least one of the one or more specific markers is a CD-characterized cell membrane structure.

23. The pseudo-tissue of claim 1, wherein said cells of at least two different cell populations are stabilized prior to fixation, wherein said stabilization is at least one member selected from the group consisting of a microwave heating stabilization and a freezing stabilization.

24. The pseudo-tissue of claim 1, wherein the marker is a hematological marker.

25. The pseudo-tissue of claim 1, wherein the marker is a cell membrane constituent.

26. The pseudo-tissue of claim 1, wherein the marker is a nuclear bound receptor.

27. The pseudo-tissue of claim 1, wherein the marker is an infectious agent.

28. A method for the production of a pseudo-tissue, comprising the steps of:
   (a) selecting a first isolated cell population that comprises cells that are substantially identical to each other with respect to the number of one or more specific marker(s);
   (b) selecting at least one additional isolated cell population that comprises cells that are substantially identical to each other with respect to the number of one or more specific marker(s), wherein said cells of said additional cell population differ from the cells of said first cell population with respect to one or more of said specific marker(s);
   (c) mixing the first cell population with the additional cell population to thereby form a substantially homogeneous cell mixture, wherein the ratio between the cells of the first cell population and cells of the additional cell population is known; and
   (d) incorporating the substantially homogeneous cell mixture into a matrix to thereby form the pseudo-tissue, wherein said cells of the first cell population and the additional cell population are fixed prior to or after forming the cell mixture and prior to incorporation into the matrix.

29. The method of claim 28, wherein the number of cells in the first cell population relative to the number of cells in the second cell population is predetermined.

30. The method of claim 29, wherein a ratio between cells of the first cell population and cells of the second cell population in the substantially homogeneous cell mixture is from $1:10^9$ to $10^9:1$.

31. The method of claim 29, wherein a ratio between cells of the first cell population and cells of the second cell population in the substantially homogeneous cell mixture is from 1:20 to 20:1.

32. The method of claim 28, further comprising the step of cutting the matrix with the cells into sections.

33. The method of claim 32, wherein the matrix is cut into sections having a thickness of up to about 100 μm.

34. The method of claim 32, wherein the matrix is cut into sections between 50 nm and 100 μm.

35. The method of claim 32, wherein the matrix is cut into sections between 80 and 120 nm.

36. The method of claim 32, wherein the matrix is cut into sections between 2 and 5 μm.

\* \* \* \* \*